(12) United States Patent
Wang et al.

(10) Patent No.: US 11,266,363 B2
(45) Date of Patent: Mar. 8, 2022

(54) ENERGY-SENSITIVE MULTI-CONTRAST COST-EFFECTIVE CT SYSTEM

(71) Applicant: RENSSELAER POLYTECHNIC INSTITUTE, Troy, NY (US)

(72) Inventors: Ge Wang, Loudonville, NY (US); Wenxiang Cong, Albany, NY (US)

(73) Assignee: Rensselaer Polytechnic Institute, Troy, NY (US)

(*) Notice: Subject to any disclaimer, the term of this patent is extended or adjusted under 35 U.S.C. 154(b) by 771 days.

(21) Appl. No.: 15/999,466

(22) PCT Filed: Feb. 17, 2017

(86) PCT No.: PCT/US2017/018456
§ 371 (c)(1),
(2) Date: Aug. 17, 2018

(87) PCT Pub. No.: WO2017/143247
PCT Pub. Date: Aug. 24, 2017

(65) Prior Publication Data
US 2021/0204890 A1    Jul. 8, 2021

Related U.S. Application Data

(60) Provisional application No. 62/296,204, filed on Feb. 17, 2016.

(51) Int. Cl.
*A61B 6/00* (2006.01)
*A61B 6/04* (2006.01)
*A61B 6/03* (2006.01)

(52) U.S. Cl.
CPC .............. *A61B 6/4291* (2013.01); *A61B 6/03* (2013.01); *A61B 6/0407* (2013.01); *A61B 6/483* (2013.01);
(Continued)

(58) Field of Classification Search
CPC ....... A61B 6/4291; A61B 6/032; A61B 6/508; A61B 6/0407; A61B 6/484; A61B 6/03; A61B 6/483
See application file for complete search history.

(56) References Cited

U.S. PATENT DOCUMENTS 9,134,259 B2    9/2015 Huang et al.
2003/0068010 A1*    4/2003 Lentfer ............ G01N 23/20016
378/81
(Continued)

FOREIGN PATENT DOCUMENTS

CN    201191275 Y * 2/2009 ............. A61B 6/484
JP    2013116313    6/2013

OTHER PUBLICATIONS

International Search Report and Written Opinion, International Patent Application No. PCT/US2017/018456, dated May 18, 2017.

*Primary Examiner* — Chih-Cheng Kao
(74) *Attorney, Agent, or Firm* — Murtha Cullina LLP; Anthony P. Gangemi

(57) ABSTRACT

Systems and methods for obtaining scattering images during computed tomography (CT) imaging are provided. Two gratings or grating layers can be disposed between the object to be imaged and the detector, and the gratings or grating layers can be arranged such that primary X-rays are blocked while scattered X-rays that are deflected as they pass through the object to be imaged reach the detector to generate the scattering image.

29 Claims, 9 Drawing Sheets

(52) U.S. Cl.
CPC .............. *A61B 6/484* (2013.01); *A61B 6/508* (2013.01); *A61B 6/032* (2013.01)

(56) References Cited

U.S. PATENT DOCUMENTS

| | | | |
|---|---|---|---|
| 2010/0191145 A1* | 7/2010 | Lafferty | A61B 10/0096 600/562 |
| 2010/0220832 A1 | 9/2010 | Ning et al. | |
| 2011/0235775 A1* | 9/2011 | Tada | A61B 6/585 378/36 |
| 2012/0057676 A1* | 3/2012 | Koehler | G21K 1/06 378/85 |
| 2012/0099705 A1* | 4/2012 | Murakoshi | A61B 6/4291 378/85 |
| 2012/0163554 A1* | 6/2012 | Tada | A61B 6/4291 378/154 |
| 2012/0288056 A1 | 11/2012 | Murakoshi et al. | |
| 2013/0230135 A1 | 9/2013 | Hoshino et al. | |
| 2015/0124927 A1* | 5/2015 | Koehler | G01N 23/20083 378/19 |
| 2017/0014091 A1* | 1/2017 | Mertelmeier | A61B 6/484 |

* cited by examiner

ENERGY-SENSITIVE MULTI-CONTRAST COST-EFFECTIVE CT SYSTEM

CROSS-REFERENCE TO RELATED APPLICATION

This application is a national stage application of International Patent Application No. PCT/US2017/018456, filed Feb. 17, 2017, which claims the benefit of U.S. Provisional Application Ser. No. 62/296,204, filed Feb. 17, 2016, which is incorporated herein by reference in its entirety, including any figures, tables, and drawings.

STATEMENT REGARDING FEDERALLY SPONSORED RESEARCH OR DEVELOPMENT

This invention was made with government support under grant No. EB016977 awarded by the National Institutes of Health. The government has certain rights in the invention.

BACKGROUND

High-resolution X-ray assessment of lung and other tumors, in vivo or after surgical resection, has become increasingly important, as are imaging studies of small objects such as organoids. Samples, specimens, and tissue constructs have several unique properties, including but not limited to: less issues with increased radiation dose given that they are samples instead of animals (e.g., humans); higher resolution requirements than that usually achievable in small animal in vivo studies; and richer image contrasts being desirable because attenuation-based X-ray imaging is poor in soft tissue contrast.

Based on improvements in the spatial resolution and temporal resolution of micro computed tomography (CT), the applications of this technology are becoming more extensive. In particular, micro CT has gradually been accepted as an indispensable tool in clinical medicine as an effective measure to detect cancer specimens and solve margin positive problems. With the progress on examining surgical specimens using micro CT, it can be effective to aid a surgeon and in the processing of the specimen by a pathologist. Most related art commercial micro CT scanners have only one imaging mode, which is called absorption contrast imaging. The X-ray absorption coefficient is roughly proportional to the fourth power of the atomic number, and that is why X-rays lack sufficient power to observe biological soft tissues. Due to this disadvantage, alternative approaches have been investigated to enhance the contrast of soft tissues. One option is to make use of diverse contrast agents containing high-Z elements. Another option is to compare different signals with traditional absorption contrast imaging. X-ray phase contrast imaging can get phase shift information when X-rays transmit through the object. Existing techniques for micro CT and other types of CT imaging all have drawbacks, though.

BRIEF SUMMARY

Embodiments of the subject invention provide novel and advantageous systems and methods for obtaining scattering images (e.g., small angle scattering images or dark field images) during computed tomography (CT) imaging (e.g., X-ray CT imaging). Two gratings or grating layers can be disposed between the object to be imaged and the detector, and the gratings or grating layers can be arranged such that primary X-rays (those that are not scattered, or deflected as they pass through the object to be imaged) are blocked (e.g., partially, mostly, or completely blocked) while scattered X-rays (e.g., small angle scattering X-rays) that are deflected as they pass through the object to be imaged reach the detector to generate the scattering image (e.g., small angle scattering image or dark field image). This can lead to high-resolution, accurate dark field images that can have many important applications, including identification of cancer tissue in an animal, such as a mammal (e.g., a human). Compared to related art imaging systems and methods, systems and methods of embodiments of the subject invention are relatively efficient, inexpensive, easy to use, fast in data acquisition, and/or small in size. Energy-sensitive, multi-contrast cost-effective CT systems are provided herein, and can be termed EMCC or E=MC$^2$ systems for short.

In an embodiment, a system for performing CT scattering imaging can comprise: an X-ray source; a detector for detecting X-ray radiation; a first grating layer disposed between the detector and the radiation source; and a second grating layer disposed between the first grating layer and the detector. The first grating layer and the second grating layer can be disposed such that, during imaging, non-scattered radiation is blocked from reaching the detector and at least a portion of scattered radiation is able to pass through the first grating layer and the second grating layer to the detector.

In another embodiment, a method for performing CT scattering imaging can comprise: providing an object to be imaged; and using a CT scattering imaging system as described herein to perform CT scattering imaging on the object. The object is positioned between the radiation source and the first grating during imaging.

DETAILED DESCRIPTION

Figure 1:
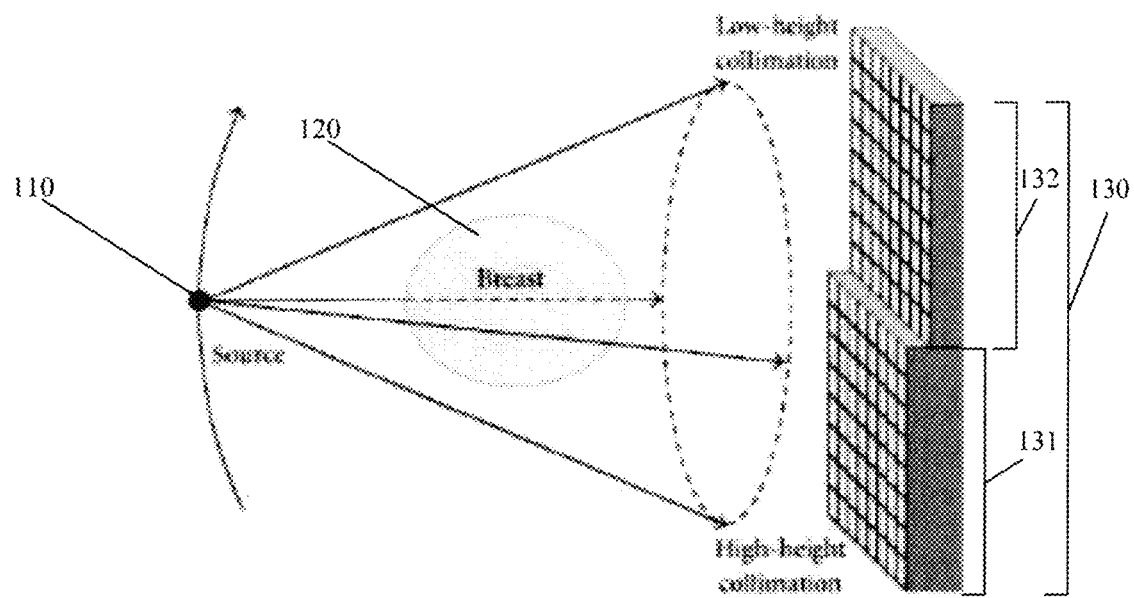
FIG. 1 shows a schematic view of a detection system with varying height collimations according to an embodiment of the subject invention.

Embodiments of the subject invention provide novel and advantageous systems and methods for obtaining scattering images (e.g., small angle scattering images or dark field images) during computed tomography (CT) imaging (e.g., X-ray CT imaging). Two gratings or grating layers can be disposed between the object to be imaged and the detector, and the gratings or grating layers can be arranged such that primary X-rays (those that are not scattered, or deflected as they pass through the object to be imaged) are blocked (e.g., partially, mostly, or completely blocked) while scattered X-rays (e.g., small angle scattering X-rays) that are deflected as they pass through the object to be imaged reach the detector to generate the scattering image (e.g., small angle scattering image or dark field image). This can lead to high-resolution, accurate dark field images that can have many important applications, including identification of cancer tissue in an animal, such as a mammal (e.g., a human). Compared to related art imaging systems and methods, systems and methods of embodiments of the subject invention are relatively efficient, inexpensive, easy to use, fast in data acquisition, and/or small in size.

Although phase contrast imaging has been studied since the early 1990's, no related art techniques had the potential to be extensively used in medicine or industry until the emergence of X-ray phase imaging systems using transmission grating optics based on Talbot interferometry or Talbot-Lau interferometry. Three types of reconstruction images can be obtained using phase contrast imaging systems, including an absorption image, a differential phase contrast image, and a dark field image. The dark field image is crucial, and its intensity depends on the scattering. That is, as the scattering intensity increases, the dark field signal becomes stronger; though strong scattering intensity will also decrease or destroy the quality of the interference pattern and the visibility. Therefore, its phase signal will become random and disorderly and its pattern amplitude will go to zero. In general, this limitation is caused by scattering. However, the scattering signal, especially small angle scattering signal, has proved to be significant in practice. Small angle scattering has been previously studied as this type of scattering can reflect the inner structure information of the scanned object at a molecular level. When cancer invades tissues, the tissue will change at the molecular level, and that is why scattering imaging has great potential in pathology when used for cancer detection.

Pathology was previously used only to determine whether cancer tissue was of the small cell or non-small cell type. Now, it is necessary to obtain as much information on tumor characteristics as possible, which is pivotal for optimizing clinical decision-making. Organoids of size greater than 1 millimeter (mm) are emerging, and adaption of micro computed tomography (micro CT) to organoids is useful, for example when attenuation, diffraction, and scattering signals are combined in an X-ray energy sensitive fashion. These major needs mean that significant improvements to X-ray CT technologies for characterization of small objects (e.g., spleen, breast, prostate, lung, and other cancer specimens) are needed. Rapid analysis of cancer margins during surgery while the patient is still under anesthesia could inform the surgeon how to best proceed. However, no such related art technique exists, as histopathology can take days. Also, the role of tumor characterization places an emphasis on therapy and prognosis, and especially relevant are three-dimensional (3D) structures including tumor vasculature, which is important for anti-angiogenic therapies, and heterogeneity. Systems and methods of embodiments of the subject invention can be scaled up for in vivo imaging as well, such as over a region of interest.

The development of high-resolution and high-content imaging (e.g., X-ray imaging) techniques are of great importance in the biomedical field and materials field, among many others. Cancer imaging is a major application, primarily because small angle scattering (also referred to as dark field) signals can differentiate benign and malignant tumors. Related art X-ray methods that use gratings are not ready for routine use because they are expensive, hard to use, slow in data acquisition, and very large. Systems and methods of embodiments of the subject invention solve many of these issues.

Also, related art scattering imaging techniques are based on conventional slot scan, which exploits multiple anti-scatter grids and double detectors. This kind of system can obtain scattering signals at a characteristic angle, but it cannot obtain small angle scattering signals and its scanning efficiency is very low. Embodiments of the subject invention provide imaging systems and methods that address the limitations of related art techniques, particularly imaging systems and methods for scattering imaging (e.g., small angle scattering imaging). Such systems and methods can be used to obtain dark field images. In many embodiments, two gratings or two layers of gratings can be used, and primary X-rays (i.e., those that are not deflected as they pass through the object to be imaged) can be partially, mostly, or completely blocked while small angle scattering X-rays can reach the detector behind the gratings or grating layers.

In many embodiments, a system includes a radiation source (e.g., an X-ray radiation source), at least two gratings or grating layers, and a detector. The gratings or grating layers are positioned such that they are between an object to be imaged and the detector during imaging. The at least two gratings or grating layers are disposed and/or configured such that primary radiation (e.g., primary X-rays) passing through the object to be imaged during imaging are blocked by the gratings or grating layers and scattering radiation (e.g., scattering X-rays) pass through to the detector. The gratings or grating layers can be positioned such that only scattering radiation of a certain angle or a minimum (or maximum) angle is allowed to pass through to the detector. In this way, the final image (e.g., after image reconstruction) is an image of only the scattering radiation. For example, the obtained image is a small angle scattering image or a dark field image. Small angle scattering is typically scattering of 10° or less, though this is not intended to be a limiting value for all small angle scattering discussed herein; a person of ordinary skill in the art would understand the term "small angle scattering" in the context of CT imaging and would understand what angles would be included.

FIG. 1 shows a schematic view of a detection system with varying height collimations according to an embodiment of the subject invention. Referring to FIG. 1, the system can include a radiation source 110, a portion for the object 120 to be imaged, and a collimator 130. The radiation source 110 can be an X-ray source, such as an X-ray tube or a microfocus X-ray source, though embodiments are not limited thereto. The portion for the object 120 to be imaged can be, for example, an object table, though embodiments are not limited thereto. An X-ray detector can also be included, separated from the collimator 130 or having the collimator 130 attached thereto. One or more phase gratings (not shown in FIG. 1) can optionally be present. The collimator 130 can be implemented with one or more absorption gratings (e.g., X-ray absorption gratings). Each grating can be an array (see, e.g., FIG. 2) and can include one or more absorbing heavy metals, such as gold, lead, or tungsten, though embodiments are not limited thereto. One-dimensional (1D) and two-dimensional (2D) absorption gratings can be fabricated, for example, in a process involving photolithography, deep etching into a substrate, and deposition (e.g., electroplating) of a heavy metal (e.g., gold) on the substrate, or using other processes. The period of each absorption grating can be designed by balancing image resolution, signal-to-noise ratio, imaging time, and other factors. The height of each absorption grating can be designed for optimal extraction of X-ray small-angle scattering signals.

Though the object 120 to be imaged is labeled in FIG. 1 as "breast" tissue, this is for exemplary purposes only and should not be construed as limiting. The object 120 can be any object that can be imaged using CT imaging. During imaging, the object 120 to be imaged can be rotated and/or the radiation source 110 and the detector can be rotated around the object 120 while the object 120 remains stationary. For example, for in vivo imaging such as organoids in a bioreactor, it may be convenient to keep the object 120 stationary while both the detector and the radiation source 110 are rotated around the object 120 during data acquisition. As another example, for ex vivo imaging, it may be convenient to rotate a sample/specimen object 120 while the radiation source 110 and the detector are fixed. The imaging system can be designed to acquire dark-field images alone or both attenuation and dark-field images to reveal subtle variations within the soft tissue, especially in high contrast between healthy and malignant tissues.

The detector of a system of the subject invention can be, for example, a photon-counting detector (e.g., for multi-energy imaging) or a current integrating detector (e.g., for grey-scale or dual-energy imaging), though embodiments are not limited thereto. A photon-counting detector can acquire attenuation and small-angle scattering data in different energy bins, which gives richer contrast information and is can further improve the signal-to-noise ratio for material-specific imaging, allowing the differentiation and classification of tissue types and contrast agents.

In some embodiments, the use of a phase grating can introduce interference patterns upon a detector surface. When used in a system as discussed herein, a phase grating can help improve imaging performance. A phase grating used in a system of the subject invention can have electrical modulation capability. The piezoelectric effect can be utilized to make a phase grating (e.g., an X-ray phase grating). The piezoelectric effect is used in many existing products such as lighters, loudspeakers, and signal transducers. Piezoelectric materials include crystals and ceramics, among others. The most well-known piezoelectric material is quartz ($SiO_2$). The inverse piezoelectric effect causes a change in thickness of a proper material when an electrical voltage is applied. For example, piezoelectric material can be cut into sheets with thickness equal to a fraction of a period of the phase grating. Each piezoelectric piece can be independently connected to a voltage source such that its height can be electronically changed. By programming the voltage sources, the structures can introduce a phase shift of, for example, $\pi/2$. In addition to the piezoelectric effect, other effects such as electronically controlled polarization effects could also be utilized for the same purpose. As a result, some piezoelectric elements can be assembled together to form a piezoelectric sheet as a phase grating under electronic control. With this phase grating, the phase-stepping scan can be implemented by changing the electric field, and this control method can achieve more accurate and stable phase-stepping than the mechanical method. The phase grating can have functionality for modulation of small angle scattering signals so that the dark field measurement can be more informative. That is, with such a phase grating, some blocked small angle scattering signals can be detected.

For a pathological sample, image resolution of related art micro CT is limited. In some embodiments, image resolution of a spectral X-ray imaging camera can be enhanced by partially blocking each detector element with an absorption grating, which is commonly used for Talbot-Lau interferometry. After acquiring X-ray data at an initial grating-detector configuration, the grating is shifted to expose previously blocked portions or patterns so that each measurement contains new information. Here, the translation of the absorption grating can be replaced by the translation or modulation of a phase grating. In this way, multiple sets of projection data can be acquired for higher resolution imaging with a lower resolution detector. All the data can then be combined and subsequently reconstructed using an iterative algorithm. Although this methodology leads to wasted radiation dose and increased scan time, pathological micro CT applications are much less sensitive to radiation dose, and demand higher resolution for more detailed analyses than in preclinical and clinical applications.

Referring again to FIG. 1, in an embodiment, a collimator 130 can include two absorption gratings or absorption grating layers having different heights. The first absorption grating or grating layer 131 has a first height $H_1$, and the second absorption grating or grating layer 132 has a second height $H_2$ ($H_1 < H_2$). The overall height $H_2$ of the collimator 130 height can be very large to achieve an optimal anti-scattering effect, and the first height $H_1$ of the first absorption grating or grating layer 131 can be chosen to be optimized for as high a signal-to-noise ratio as possible. If the radiation source 110 and the detector are rotated around an object 120 over a range of 360°, each radiation pencil beam transverses a path through the object 120 twice in opposite directions. One measurement can be recorded with the second grating 132 of the larger height $H_2$, and the other measurement can be taken with the first grating 131 of the smaller height $H_1$. In this way, two data points are available corresponding to the linear path through the object, with and without significant dark field components, respectively. Therefore, the difference between two data gives the small-angle scattering information, as shown in FIG. 1. The processing and reconstruction of these paired datasets can produce dark-field images, in addition to traditional transmission images. For cone beam X-ray imaging, the two datasets corresponding to each X-ray beam can be established by CT re-binning and correction techniques, such as the well-known cosine correction method used in the generalized FDK (Feldkamp-Davis-Kress) reconstruction.

Figure 2:
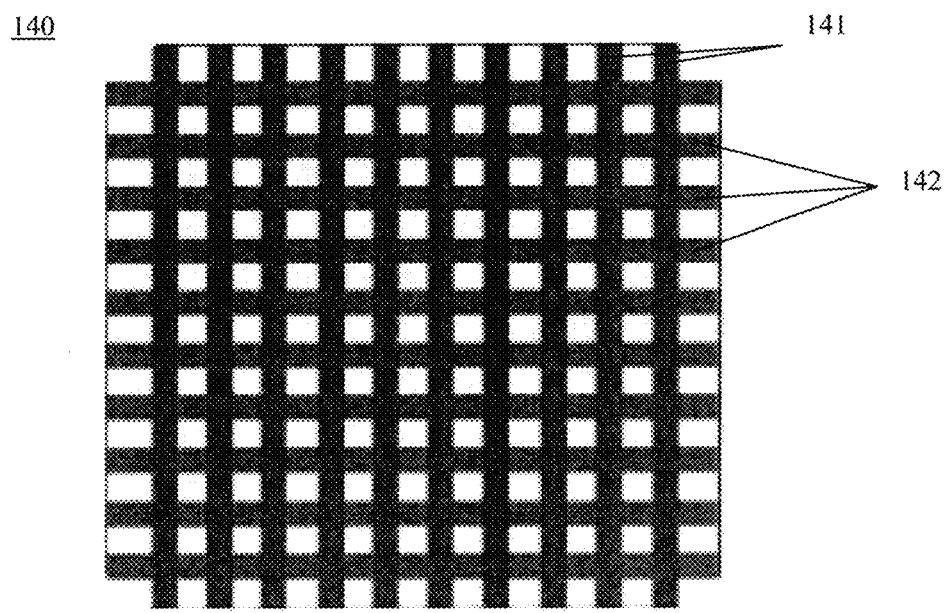
FIG. 2 shows a two-dimensional (2D) grating made from two one-dimensional (1D) gratings.
Figure 3:
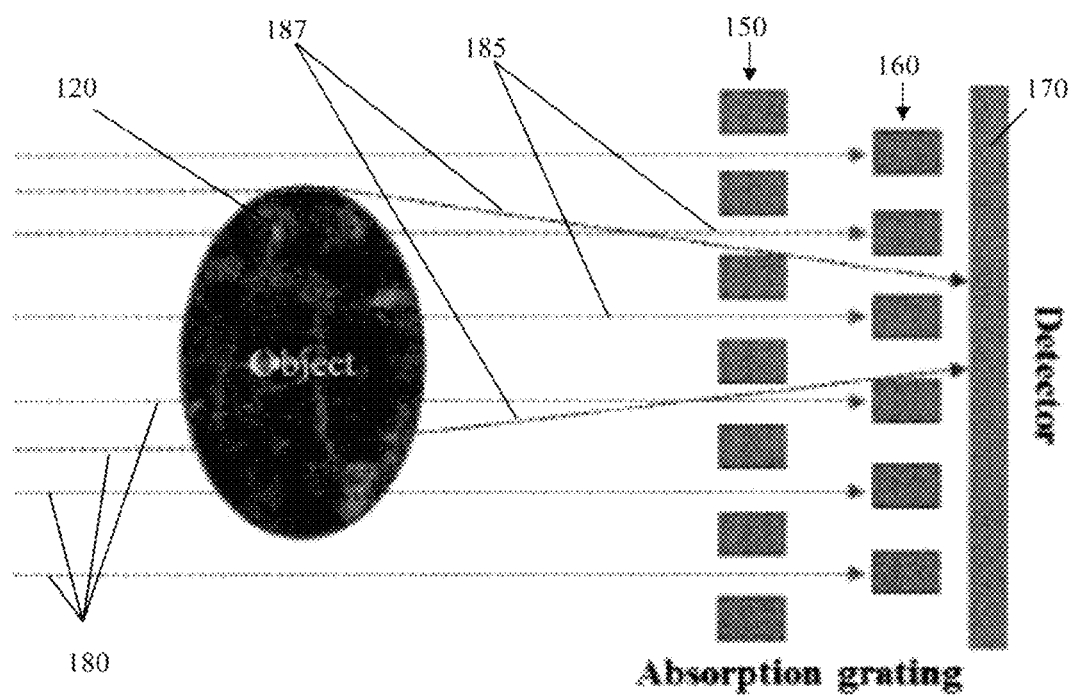
FIG. 3 shows a cross-sectional view of a detection system with two gratings according to an embodiment of the subject invention.

Several schemes can be used for direct measurement of dark field views with 1D gratings, 2D gratings, or a combination thereof. For example, a 2D absorption grating effect can be obtained with two 1D gratings, as shown in FIG. 2. Referring to FIG. 2, a vertical (as depicted) 1D grating 141 can be combined with a horizontal (as depicted) 1D grating 142 to obtain a 2D grating 140. This can effectively block all large or moderate angle scattering signals, and only let primary beams and small angle scattering signals through. Then, the openings can be blocked with another absorption grating, as shown in FIG. 3. The 1D gratings 141,142 can be of the same material or different materials.

FIG. 3 shows a cross-sectional view of a detection system with two gratings according to an embodiment of the subject invention. Referring to FIG. 3, radiation 180 can be provided to the object 120 to be imaged, resulting in primary radiation 185 and scattering radiation 187 after passing through the object 120. At least two absorption gratings can be used to absorb the primary radiation 185 (including provided radiation 180 that does not pass through the object 120) such that it does not reach the detector 170. For example, a first grating 150 and a second grating 160 can be used to absorb the primary radiation 185 (including provided radiation 180 that does not pass through the object 120). The gratings 150,160 can be positioned such that scattering radiation 187 can pass through to the detector 170 to be present in the obtained image. Appropriate separations among gratings 150,160 and the detector 170 are parameters for adjustment, in addition to grating parameters such as period, duty cycle, and aspect ratio. That is, the absorbing lines of the gratings 150,160 can overlap to completely block primary beams 185 (including provided radiation 180 that does not pass through the object 120). For example, the width of each line of the second grating 160 can be the same as the space between lines of the first grating 150, though embodiments are not limited thereto. The width of each line of each grating 150,160, the spacing between lines for each grating 150,160, the distance between the first 150 and second 160 gratings, and the distance between the second grating 160 and the detector 170 can all be adjusted as desired to allow scattering radiation of a particular angle, angle range, minimum angle, or maximum angle through to the detector. In further embodiments, additional absorption gratings can be provided. Any or all of the first 150, second 160, and any additional gratings present can be of the type shown in FIG. 2, though embodiments are not limited thereto.

Figure 6:
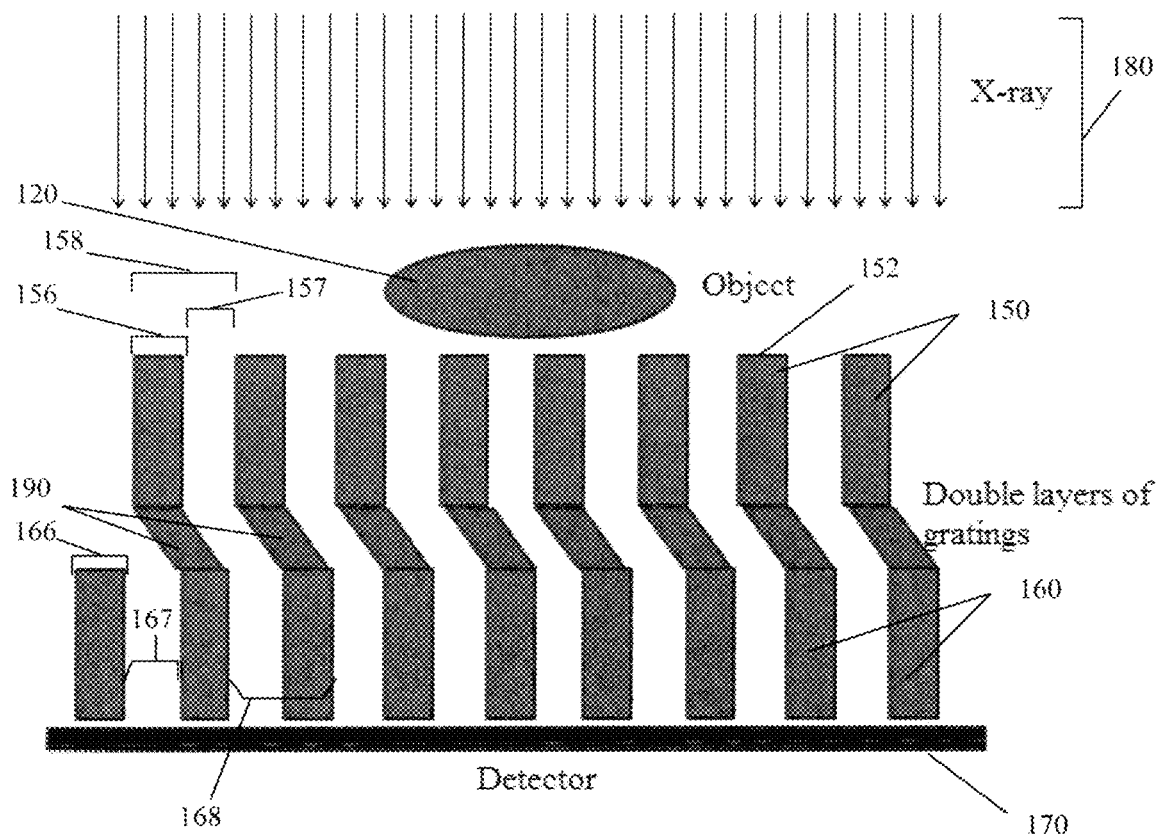
FIG. 6 shows a cross-sectional view of a detection system with two gratings according to an embodiment of the subject invention.

FIG. 6 also shows a cross-sectional view of a detection system with two gratings according to an embodiment of the subject invention. Referring to FIG. 6, this embodiment is similar to that shown in FIG. 3. Blocking structures 190, which can be referred to as septa, can be provided between the first 150 and second 160 gratings in a slanted or angled orientation with respect to the incident surface 152 of the first grating 150. The blocking structures 190 can be made of any suitable material, including but not limited to the same material as the first and/or second gratings. The blocking structures 190 can inhibit or prevent crosstalk between neighboring cells 158,168, where a cell 158,168 includes one line 156,166 and one adjoining space 157,167 in a grating 150,160.

Figure 7:
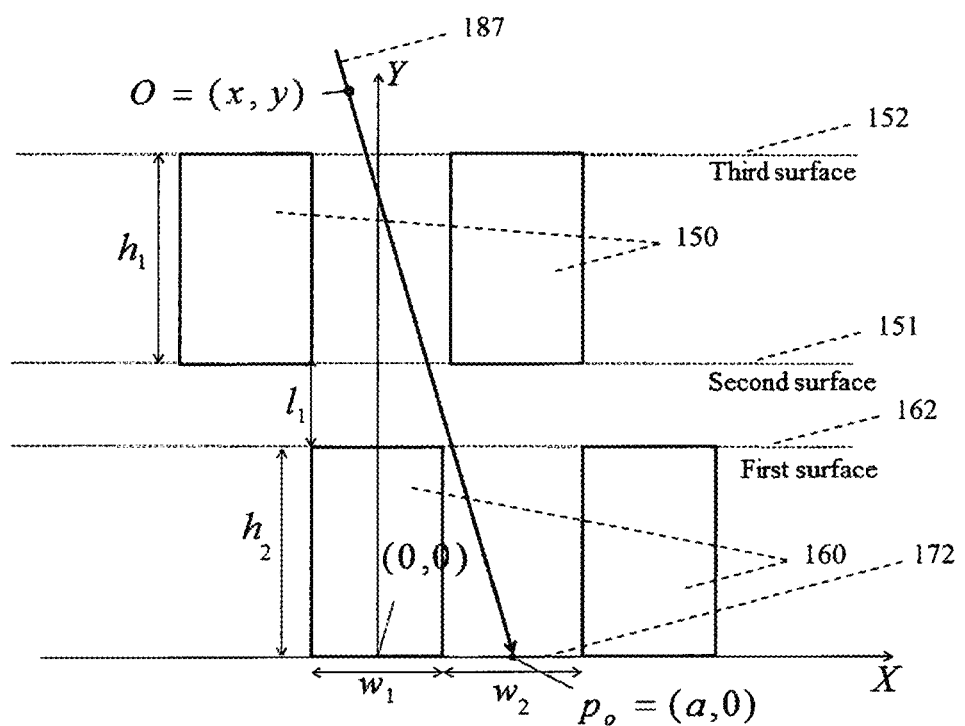
FIG. 7 shows a cross-sectional view of gratings of a detection system according to an embodiment of the subject invention.

FIG. 7 shows a cross-sectional view of gratings of a detection system according to an embodiment of the subject invention, with parameters for changing the scattering radiation angles allowed to pass to the detector. Referring to FIG. 7 (and FIG. 6 again), each cell 158,168 of the grating 150,160 contains two parts: solid part or line 156,166; and hollow part or adjoining empty space 157,167. The heights of the first 150 and second 160 gratings are $h_1$ and $h_2$, respectively. The widths of the solid part 166 and hollow part 167 of the second grating 160 are $w_1$ and $w_2$, respectively. Although not shown, the width of the solid part 156 and hollow part 157 of the first grating 150 could also be considered; the width of the solid part 156 of the first grating 150 can be the same as or different from that of the second grating 160 ($w_1$), and the width of the hollow part 157 of the first grating 150 can be the same as or different from that of the second grating 160 ($w_2$). The distance between the two gratings 150,160 is $l_1$. All of these parameters can be adjusted as desired to modulate the scattering radiation angle, angle range, maximum angle, or minimum angle allowed to pass through to the detector.

In an embodiment, the heights $h_1, h_2$ of the first 150 and second 160 gratings can be the same (i.e., $h_2=h_1$), and the widths of the solid part 166 ($w_1$) and hollow part 167 ($w_2$) of the second grating 160 can be the same (i.e., $w_2=w_1$). Also, the width of the solid part 156 of the first grating 150 can be the same as that of the second grating 160 ($w_1$), and the width of the hollow part 157 of the first grating 150 can be the same as that of the second grating 160 ($w_2$, where $w_2=w_1$). The pixel size of the detector can equal the width of a cell 158,168 and can therefore be $2w_1$ such that one pixel covers one cell 158,168. In order to determine these parameters, a rectangular coordinate system can be set up as shown in FIG. 7. If a scattering ray coming from point O=(x, y) is to reach the point $p_o=(a,0)$ located on the incident surface 172 of the detector, penetrating through the three surfaces 152,151,162 is required as shown in FIG. 3 without any obstacles. Also, the following four equations need to be met simultaneously.

$$\begin{cases} \dfrac{w_1}{2} < a < \dfrac{3w_1}{2} \\ \dfrac{w_1}{2} < a + \dfrac{h_1(x-a)}{y} < \dfrac{3w_1}{2} \\ -\dfrac{w_1}{2} < a + \dfrac{(h_1+l_1)(x-a)}{y} < \dfrac{w_1}{2} \\ -\dfrac{w_1}{2} < a + \dfrac{(2h_1+l_1)(x-a)}{y} < \dfrac{w_1}{2} \end{cases} \quad (1)$$

By analyzing and simplifying the equations in equation set (1), it can be seen that if $$a > \dfrac{l_1+h_1}{h_1} w_1 + \dfrac{w_1}{2},$$

if the relationship in formula (2) below will hold, $$\dfrac{-\dfrac{w_1}{2}-a}{2h_1+l_1} y + a < x < \dfrac{\dfrac{w_1}{2}-a}{h_1+l_1} y + a \quad (2)$$

Otherwise, the relationship in formula (3) will hold, $$\dfrac{\dfrac{w_1}{2}-a}{h_1} y + a < x < \dfrac{\dfrac{w_1}{2}-a}{h_1+l_1} y + a \quad (3)$$

Because $$\dfrac{w_1}{2} < a < \dfrac{3w_1}{2},$$

formula (3) will finally hold. In the inequality of formula (3), the receiving range of the scattering angle at the point $p_o=(a,0)$ on the detector incident surface 172 can be represented as, arctan $$\dfrac{a-\dfrac{w_1}{2}}{h_1+l_1} < \theta < \arctan \dfrac{a-\dfrac{w_1}{2}}{h_1} \quad (4)$$

From formula (4), it can be seen that $l_1$ determines the range while $h_1$ determines the size of the scattering angle. When $l_1 \ll h_1$, the receiving range of each pixel element can be represented as, $$0 < \theta < \arctan\frac{w_1}{h_1} \quad (5)$$

To make resolution desirable, the following relationship should hold, $$y\frac{w_1}{h_1} < \frac{3}{2}w_1 \quad (6)$$

Figure 4:
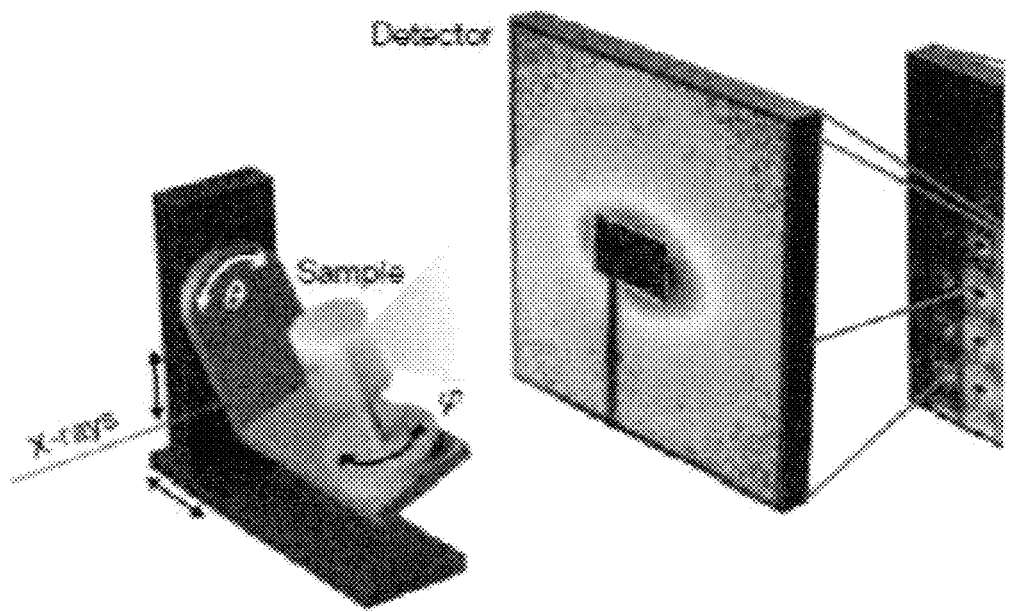
FIG. 4 shows a rotation stage for tensor dark-field tomography according to an embodiment of the subject invention.

Systems and methods of the subject invention for X-ray dark-field signal detection can be extended for tensor dark-field tomographic imaging to provide more information on structural variation and density fluctuation inside an object, allowing analysis of object structures at micro-scale and/or nano-scale with information on the orientations of these structures. The object to be imaged can be mounted on a goniometer with two or three degrees of freedom rotation on the object table between the radiation source and the grating-detector combination, as shown in FIG. 4. The orientation of the object to be imaged can be chosen arbitrarily within a wide angular range to acquire small-angle scattering from different directions. Further, from the measured dark-field images at different directions, the tensor dark-field tomographic image reconstruction can be performed to provide a scattering tensor with multiple independent structural parameters of every volumetric element in the object to be imaged. Tensor dark-field tomography can have great utility in materials science and medical diagnostics.

In some embodiments, curved gratings (absorption gratings and/or phase gratings) can be used. That is, one or more of the gratings used can be curved. An X-ray source (e.g., an X-ray tube) is commonly a point-like source, which can emit a divergent beam, for example of a cone shape. The flat-grating imaging methods are most useful in parallel-beam imaging geometry, and suffer from limitations in both the field of view and the flux of photons. Flat grating designs can be extended to curved gratings (e.g., cylindrical or spherical grating) for cone or fan beams of X-rays. The curved gratings can be configured to allow perpendicular incidence of X-rays on the gratings, thereby matching an X-ray cone well, leading to higher visibility over a larger field of view with a higher signal-to-noise ratio of dark-field images than that with flat gratings. When curved gratings are used, the remainder of the system can be the same or similar as discussed herein.

Figure 5:
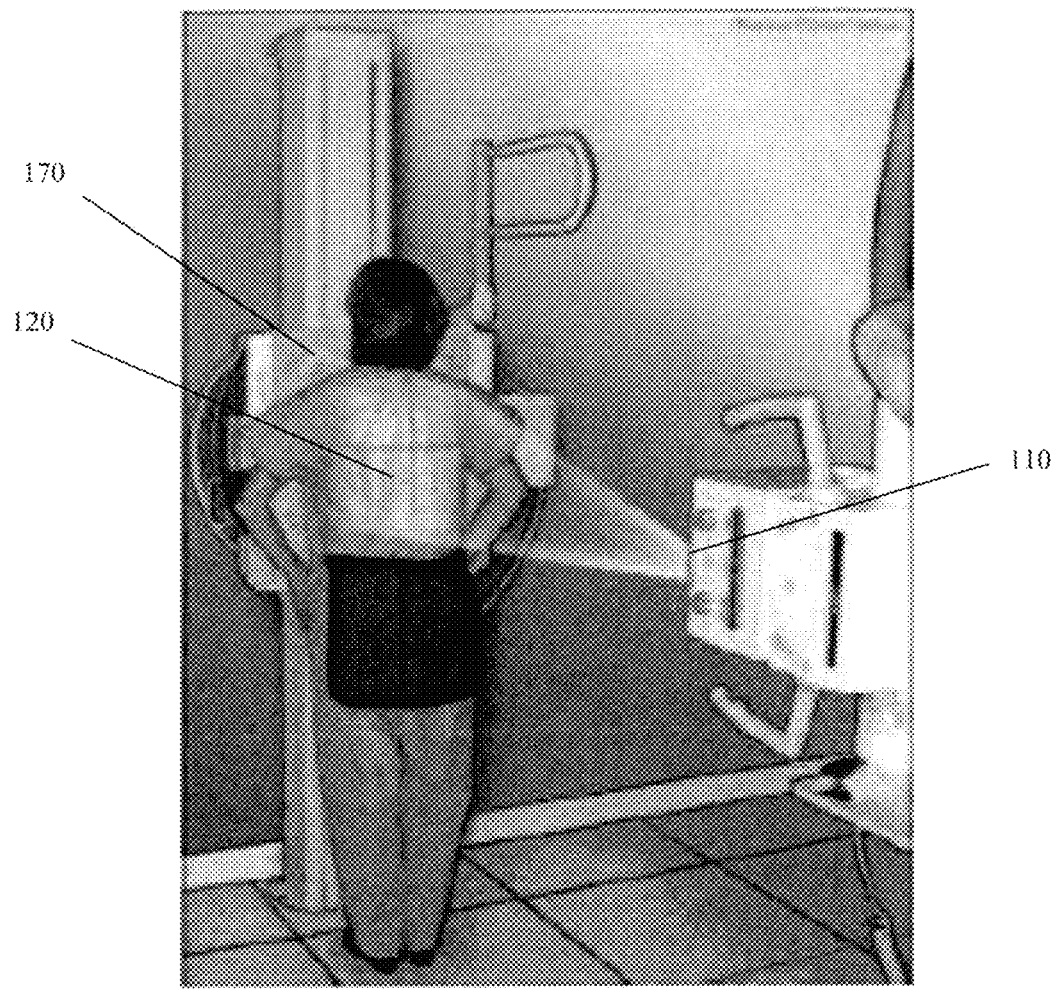
FIG. 5 shows an image of chest radiography.

Systems and methods of the subject invention for X-ray dark-field signal detection can be used, for example, in chest or breast radiography. This type of dark-field imaging is much more cost-effective than X-ray interferometry, and both can reveal subtle texture of tissues to differentiate diseased tissues from healthy tissues. For imaging of a human subject, two views can be taken: one in which the X-rays pass through the chest from the back (posterior-anterior view), and one in which the X-rays pass through the chest from one side to the other (lateral view). FIG. 5 shows an image of an example of a posterior-anterior view.

Real scattering signals are often considered to be noise in practice as they diffuse over the detector, so they cannot be extracted or detected effectively using related art methods. Systems and methods of the subject invention efficiently extract scattering signals, thereby allowing for production of small angle scattering images or dark field images that can be useful in the fields of cancer tissue identification and materials science, among others. Small angle scattering imaging can provide additional information about surgical specimens, so use of the systems and methods disclosed herein can significantly improve CT imaging (e.g., micro CT imaging). Geometric parameters of absorption gratings can be set as desired to allow scattering radiation of a certain angle, angle range, minimum angle, or maximum angle to pass through to the detector while other radiation is blocked by the gratings.

Embodiments of the subject invention can perform small angle scattering imaging, or dark-field imaging, by acquiring photons slightly deflected from the primary beam through an object to be imaged. Small-angle scattering signals reflect structural texture on length scales between 1 nanometer (nm) to several hundred nm. Such imaging can reveal subtle texture of tissues. For example, the growth of tumors causes remarkable differences on small-angle patterns from that of healthy tissue. The X-ray dark-field imaging can reveal subtle texture of tissues to differentiate diseased tissue from healthy tissue.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processer reads and executes the code and/or data stored on a computer-readable medium, the computer system and/or processer performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

Example 1

EGSnrc simulation software was used to simulate small angle scattering imaging using a system according to an embodiment of the subject invention. Monte Carlo simulations were performed on the system.

EGSnrc is a well-known simulation software whose function is to model the passage of electrons and photons through matter. Because it relies on Monte Carlo, which is the most accurate method to model the transport of radiation, the simulation results discussed herein are logical and reliable.

The gratings were composed of tungsten. The height and width of each grating cell were set to be 1 centimeter (cm) and 0.5 millimeter (mm), respectively. The dimensions of the detector were 100 mm×3 mm with a pixel size of 1 mm. The grating was aligned with the middle of the detector. The length of the gap between the two layers of the grating was 0.1 cm. The X-ray source was a parallel-beam source with an operating voltage of 20 kilovolts-peak (kVp), and there was a total of $1.28 \times 10^{10}$ photons involved in each simulation. The phantom involved was a cylindrical water phantom, with a radius of 5 mm and a height of 1 mm.

Figure 8:
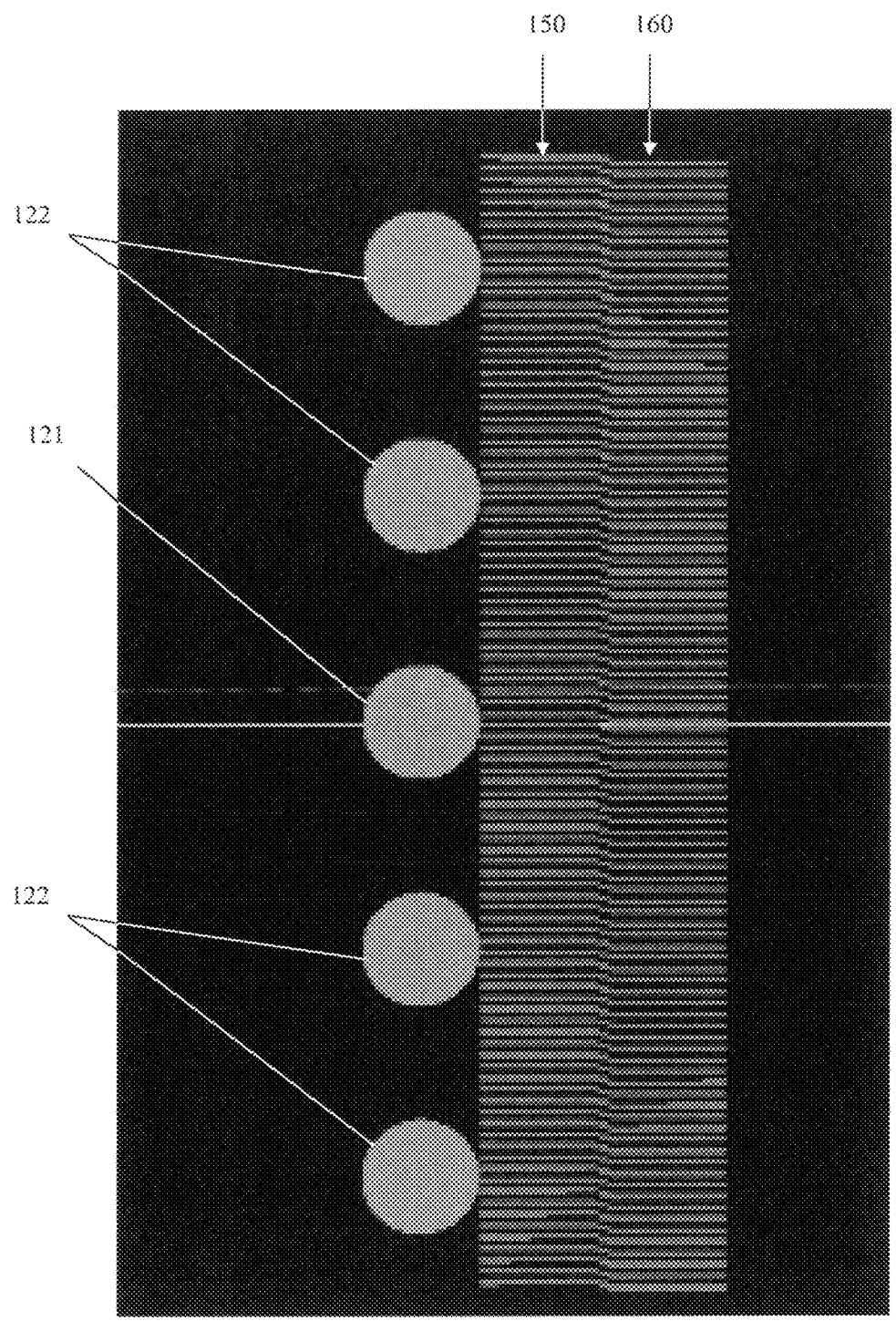
FIG. 8 shows a plan view of phantoms and gratings used in a simulation.

Referring to the experimental setup in FIG. 8, in the first simulation, five copies of the phantom 121 were used and placed equally spaced in front of the grating 150, very close to the grating 150. The simulation phantoms 121,122 were arranged as shown in FIG. 8.

Figure 9:
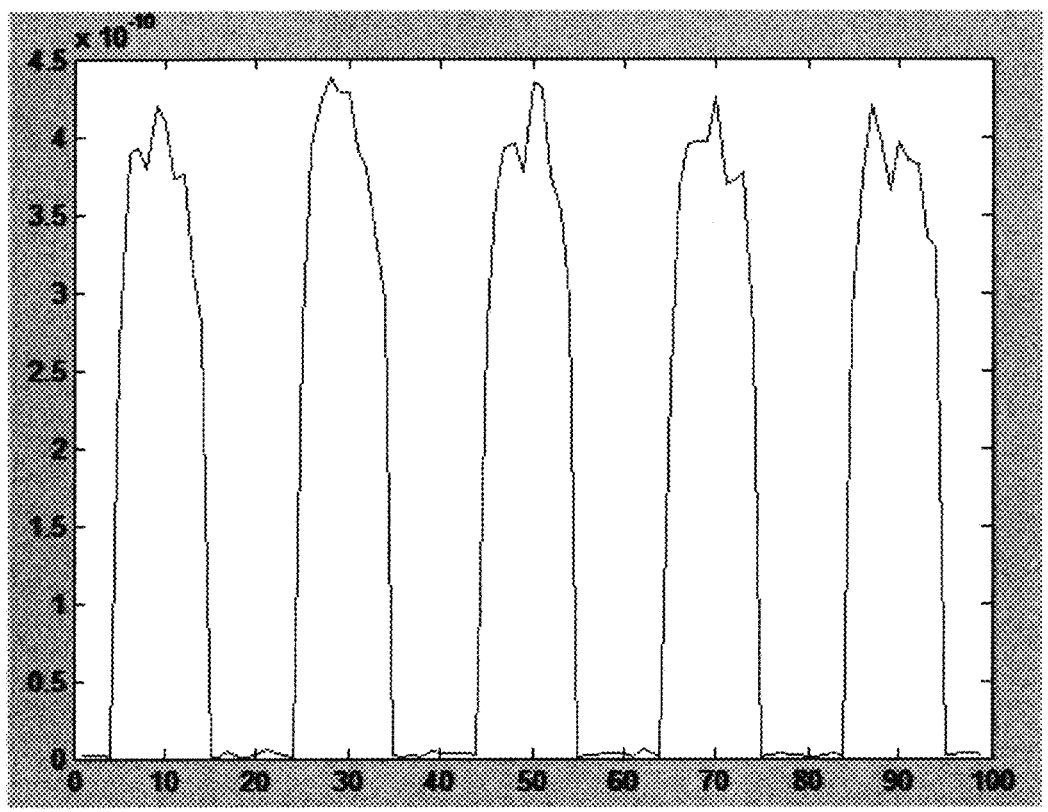
FIG. 9 shows a plot of projection data obtained from the middle of the detector in a simulation.

FIG. 9 shows a plot of projection data of the five phantoms obtained from the middle of the detector. Referring to FIG. 9, it can be seen that there are five similar peaks, which represent the five cylindrical phantoms. It can also be seen that all the peaks appear arcuate. The relationship between the incident flux and the small angle scattering intensity is as follows:

$$P_1 = I_0 \sigma(0) t \Omega \exp(-\mu t) \qquad (7)$$

where $I_0$ is the incident flux, $\sigma(0)$ is the scattering coefficient in the forward direction per unit solid angle per unit thickness of sample, t is the sample thickness, and p is the linear absorption coefficient. From this, it can be seen that the scattering intensity should be related to the distance of the X-rays passing through the phantom; the peaks in FIG. 9 are consistent with this, and the width of these peaks are the same as the diameter of the cylindrical phantom.

Example 2

Figure 10:
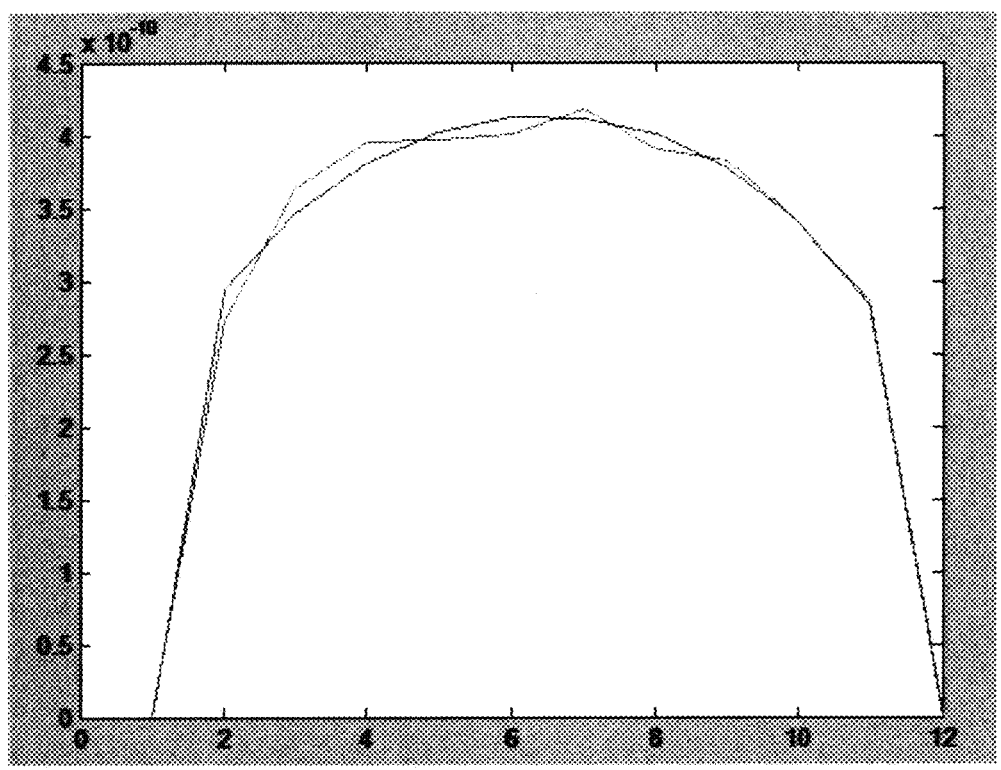
FIG. 10 shows a plot of average scattering of ten groups in a simulation.
Figure 11:
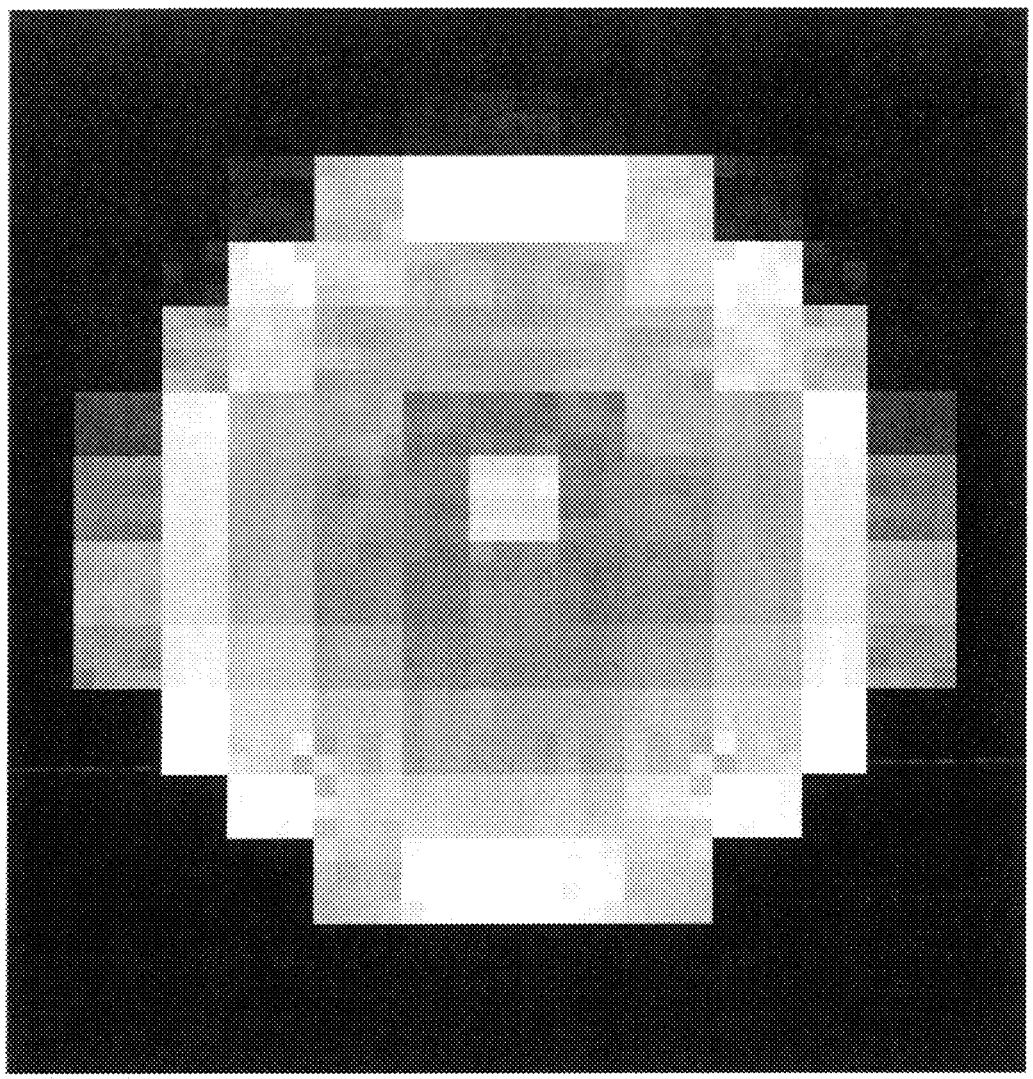
FIG. 11 shows a reconstructed image of a phantom based on scattering signal in a simulation.

A second simulation experiment was performed using the same parameters as in Example 1, but only one phantom was used. The phantom 121 was located in front of the middle of the grating 150. In order to reconstruct the scattering data, the phantom was rotated 360 degrees equiangularly around its center, and 10 groups of scattering data were acquired. The profile of the average value of these 10 groups of scattering data is shown in FIG. 10 (the line that is less smooth). It can be seen that the quadratic fit curve (the smoother line) fits well with the profile, and that means the scattering signal is effective. By the physical model to describe X-ray small angle scattering based on the principle of energy conservation, these ten groups of scattering data were used to reconstruct the cross-sectional image of the phantom 121, which is shown in FIG. 11. The shape and size of the circle in FIG. 11 is completely consistent with the phantom. This result demonstrates that the scattering imaging system can acquire the small angle scattering signal effectively.

The tested setup performed very well with the parallel beam geometry X-ray source. For fan beam and cone beam geometry sources, modifications can be made based on the specific geometric parameters; for example, curved gratings can be used.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A system for performing computed tomography (CT) scattering imaging, the system comprising:
   an X-ray radiation source;
   a detector for detecting X-ray radiation;
   a first grating layer disposed between the detector and the X-ray radiation source;
   a second grating layer disposed between the first grating layer and the detector; and
   blocking structures disposed between the first grating layer and the second grating layer, the blocking structures being configured to inhibit crosstalk between neighboring cells of the second grating layer,
   wherein the blocking structures are in direct physical contact with solid line parts of the first grating layer, respectively,
   wherein the blocking structures are in direct physical contact with solid line parts of the second grating layer, respectively, and
   wherein the first grating layer and the second grating layer are disposed such that, during imaging, non-scattered X-ray radiation is blocked from reaching the detector and at least a portion of scattered X-ray radiation is able to pass through the first grating layer and the second grating layer to the detector.

2. The system according to claim 1, wherein the system is configured such that an object to be imaged is positioned between the X-ray radiation source and the first grating layer.

3. The system according to claim 1, further comprising an object table disposed between the X-ray radiation source and the first grating and configured to have an object to be imaged placed thereon during imaging.

4. The system according to claim 1, wherein the X-ray radiation source is a micro-focus X-ray source.

5. The system according to claim 1, wherein the first grating layer has a first height and the second grating layer has a second height different from the first height.

6. The system according to claim 1, wherein the first grating layer comprises a heavy metal, and
   wherein the second grating layer comprises a heavy metal.

7. The system according to claim 1, wherein the first grating layer comprises at least one of gold, lead, and tungsten, and
   wherein the second grating layer comprises at least one of gold, lead, and tungsten.

8. The system according to claim 1, wherein the first grating layer comprises a plurality of first cells, each first cell having a solid line part, among the solid line parts of the first grating layer, and an empty space part, the empty space part of each first cell being adjacent to the solid line part of the respective first cell,
   wherein the second grating layer comprises a plurality of second cells, each second cell having a second solid line part, among the solid line parts of the second grating layer, and an empty space part, the empty space part of each second cell being adjacent to the solid line part of the respective second cell, and wherein the second grating layer is disposed such that solid parts of the second cells respectively line up at least partially with empty space parts of the first cells so that non-scattered X-ray radiation is blocked from reaching the detector during imaging.

9. The system according to claim 8, wherein the second grating layer is disposed such that the solid parts of the second cells respectively line up completely with the empty space parts of the first cells, and wherein a width of each solid part of the second cells is the same as or greater than that of each empty space part of the first cells.

10. The system according to claim 8, wherein a width of each solid part of the second cells is the same as that of each empty space part of the first cells, wherein a width of each solid part of the first cells is the same as that of each empty space part of the second cells, and wherein a width of each solid part of the second cells is the same as that of each empty space part of the second cells.

11. The system according to claim 1, wherein a distance between the first grating and the second grating is greater than a distance between the second grating and the detector.

12. The system according to claim 1, wherein the second grating is physically attached to the detector.

13. The system according to claim 1, further comprising a phase grating disposed between the detector and the X-ray radiation source.

14. The system according to claim 1, wherein the first grating layer is a curved grating layer, wherein the first grating layer has a cylindrical-type curve or a spherical-type curve.

15. The system according to claim 14, wherein the second grating layer is a curved grating, wherein the second grating layer has a cylindrical-type curve or a spherical-type curve.

16. The system according to claim 1, wherein the blocking structures are disposed in a slanted or angled orientation with respect to an incident surface of the first grating layer.

17. The system according to claim 1, wherein the system is capable of performing tensor dark field tomographic imaging, wherein the system comprises a goniometer on which an object to be imaged can be mounted, the goniometer being disposed between the X-ray radiation source and the first grating, and wherein the goniometer has at least two degrees of freedom of rotation.

18. The system according to claim 1, wherein the first grating layer is an absorption grating, and wherein the second grating layer is a separate absorption grating.

19. The system according to claim 1, wherein the first grating layer and the second grating layer are disposed such that, during imaging, non-scattered X-ray radiation is blocked from reaching the detector, scattered X-ray radiation having a scattering angle of greater than 10° is blocked from reaching the detector, and scattered X-ray radiation having a scattering angle of 10° or less is able to pass through the first grating and the second grating to the detector.

20. The system according to claim 1, wherein the system is configured to obtain a dark field image of an object to be imaged.

21. A method for performing computed tomography (CT) scattering imaging, the method comprising:

providing an object to be imaged; and using the system according to claim 1 to perform CT scattering imaging on the object, wherein the object is positioned between the X-ray radiation source and the first grating.

22. The method according to claim 21, wherein the object is kept stationary during the entire time imaging is performed, and wherein the X-ray radiation source and the detector are rotated around the object to be imaged during imaging.

23. The method according to claim 22, wherein the X-ray radiation source and the detector are rotated around the object to be imaged over a range of 360 degrees during imaging.

24. The method according to claim 21, wherein both the X-ray radiation source and the detector are kept stationary during the entire time imaging is performed, and wherein the object to be imaged is rotated during imaging.

25. The method according to claim 21, wherein the object to be imaged is an animal, is suspected of containing cancerous tissue, or combinations thereof.

26. The method according to claim 21, wherein the imaging is ex vivo imaging on a sample or specimen, wherein the object to be imaged is the sample or specimen.

27. The method according to claim 21, wherein the image obtained is a dark field image of the object.

28. The method according to claim 21, wherein the first grating layer and the second grating layer are disposed such that, during imaging, non-scattered X-ray radiation is blocked from reaching the detector, scattered X-ray radiation having a scattering angle of greater than 100 degrees is blocked from reaching the detector, and scattered X-ray radiation having a scattering angle of 100 degrees or less is able to pass through the first grating and the second grating to the detector.

29. A system for performing computed tomography (CT) scattering imaging, the system comprising:

an X-ray source;

a detector for detecting X-ray radiation;

a first grating layer disposed between the detector and the X-ray source;

a second grating layer disposed between the first grating layer and the detector; and a plurality of blocking structures disposed between the first grating layer and the second grating layer to inhibit crosstalk between neighboring cells of the second grating layer, wherein the blocking structures are in direct physical contact with solid line parts of the first grating layer, respectively, wherein the blocking structures are in direct physical contact with solid line parts of the second grating layer, respectively, and wherein the first grating layer and the second grating layer are disposed such that, during imaging, non-scattered radiation is blocked from reaching the detector and at least a portion of scattered radiation is able to pass through the first grating layer and the second grating layer to the detector.

* * * * *